(12) United States Patent
Ogawa et al.

(10) Patent No.: US 8,816,274 B2
(45) Date of Patent: Aug. 26, 2014

(54) MASS SPECTROMETER

(75) Inventors: Kiyoshi Ogawa, Kizugawa (JP); Mitsutoshi Setou, Hamamatsu (JP)

(73) Assignee: Shimadzu Corporation, Kyoto-Shi (JP)

( * ) Notice: Subject to any disclaimer, the term of this patent is extended or adjusted under 35 U.S.C. 154(b) by 38 days.

(21) Appl. No.: 13/262,217

(22) PCT Filed: Mar. 31, 2009

(86) PCT No.: PCT/JP2009/001492
§ 371 (c)(1),
(2), (4) Date: Nov. 8, 2011

(87) PCT Pub. No.: WO2010/113209
PCT Pub. Date: Oct. 7, 2010

(65) Prior Publication Data
US 2012/0104247 A1    May 3, 2012

(51) Int. Cl.
*H01J 49/04* (2006.01)
*G01N 1/06* (2006.01)
*H01J 49/00* (2006.01)
*G01N 1/28* (2006.01)

(52) U.S. Cl.
CPC .............. *H01J 49/0004* (2013.01); *G01N 1/06* (2013.01); *G01N 1/286* (2013.01); *H01J 49/0459* (2013.01)
USPC ....................................... 250/288

(58) Field of Classification Search
CPC ................................... H01J 49/0004
USPC ............................... 250/281–300
See application file for complete search history.

(56) References Cited

U.S. PATENT DOCUMENTS

| 5,498,545 | A |   | 3/1996 | Vestal |
| 5,808,300 | A | * | 9/1998 | Caprioli ................ 250/288 |

(Continued)

FOREIGN PATENT DOCUMENTS

| JP | 10513546 A | 12/1998 |
| JP | 2004219261 A | 8/2004 |

(Continued)

OTHER PUBLICATIONS

Aerni et al. 'Automated Acoustic Matrix Deposition for MALDI Sample Preparation' Feb. 1, 2006, Analytical Chemistry, vol. 78, No. 3, p. 827-834.*

(Continued)

*Primary Examiner* — Nicole Ippolito
*Assistant Examiner* — Eliza Osenbaugh-Stewar
(74) *Attorney, Agent, or Firm* — Bingham McCutchen LLP

(57) ABSTRACT

A sample stage (2) on which a sample (4) is placed can be reciprocally moved along a guide (5) by a driving mechanism (6). A cutter (9) which is moved in an X-Y plane by a driving mechanism (10) is placed at a sample cutting position (B). When the sample stage (2) is moved to the sample cutting position (B) and the cutter is driven with the height of the sample stage (2) being appropriately adjusted, an upper portion of the sample 4 is horizontally cut off with a predetermined thickness and a new sample analysis surface which was inside the sample 4 is exposed. Hence, by repeating a mass analysis for a predetermined measurement area at an analysis position (C) and a partial cutting of the sample 4 at the sample cutting position (B), it is possible to achieve a three-dimensional mass analysis imaging of the sample (4) without removing the sample (4) from the sample stage (2).

16 Claims, 5 Drawing Sheets

(56) References Cited

U.S. PATENT DOCUMENTS

| | | |
|---|---|---|
| 2003/0073145 A1 | 4/2003 | Caprioli |
| 2004/0026630 A1* | 2/2004 | Mohun et al. ............... 250/458.1 |
| 2004/0232330 A1* | 11/2004 | Uenishi et al. ................ 250/306 |
| 2007/0114388 A1* | 5/2007 | Ogawa et al. ................. 250/288 |
| 2008/0073509 A1* | 3/2008 | Ban et al. ..................... 250/288 |

FOREIGN PATENT DOCUMENTS

| | | | |
|---|---|---|---|
| JP | 2005539199 A | 12/2005 | |
| JP | 2007066533 A | 3/2007 | |
| JP | 2007157353 A | 6/2007 | |
| JP | 2007271612 A | 10/2007 | |
| JP | 2009025268 A | 2/2009 | |
| WO | 9603768 A1 | 2/1996 | |
| WO | 03034024 A2 | 4/2003 | |

OTHER PUBLICATIONS

Kiyoshi Ogawa et al., "Research and Development of Mass Microscope" (with English abstract) Shimadzu Review, Shimadzu Corporation, vol. 62, Nos. 3-4, pp. 125-135, Mar. 31, 2006.

Takahiro Harada et al., "Biological Tissue Analysis using Mass Microscope" (with English abstract) Shimadzu Review, Shimadzu Corporation, vol. 64, Nos. 3-4, pp. 139-146, Apr. 24, 2008.

Japanese language international preliminary report on patentability dated Nov. 15, 2011 and its English language translation for corresponding PCT application PCT/JP2009/001492.

Japanese language office action dated Jul. 17, 2012 and its English language translation issued in corresponding Japanese application 2011506841.

* cited by examiner

MASS SPECTROMETER

CROSS-REFERENCE TO THE RELATED APPLICATIONS

The present application is a national stage of international application No. PCT/JP2009/001492, filed on Mar. 31, 2009, the entire contents of which are incorporated herein by reference.

TECHNICAL FIELD

The present invention relates to a mass spectrometer. More specifically, it relates to a mass spectrometer, called a mass microscope or an imaging mass spectrometer, capable of performing a mass analysis for a two-dimensional area on a sample.

BACKGROUND ART

In order to observe the morphology of a sample, such as a biological tissue, and simultaneously measure the distribution of the molecules existing in a specified area on the sample, apparatuses called a mass microscope or an imaging mass spectrometer have been developed (refer to Patent Documents 1 and 2, Non-Patent Documents 1 and 2, and other documents). These apparatuses require no grinding or crushing of the sample (as required in conventional apparatuses) and hence are capable of mapping molecules included in any area on the sample specified based on a microscopic observation while almost completely maintaining the original morphology of the sample. These apparatuses are expected to be used, for example, to obtain distribution information on the proteins included in a living cell, particularly in the fields of biochemistry, medical care, pharmaceutical chemistry, and other fields.

The ionization method mainly used in such a mass microscope is a matrix-assisted laser desorption ionization (MALDI) method or a secondary ion mass spectrometry (SIMS) method. In some cases, a desorption electrospray ionization (DESI) method is alternatively used. In any methods, in analyzing a sample such as a biological tissue, the sample is sliced and attached to a sample plate. Then, a pretreatment such as a matrix coating is performed according to necessity and the sample is set to the apparatus. A small focused laser beam or ion beam is delivered onto the sample and the irradiation position is changed thereon, thereby performing a mass analysis for a specified area on the sample to obtain, for example, a mass analysis result image for a specific mass-to-charge ratio.

With the previously described conventional measurement methods, a mass analysis result image can be obtained for a specific mass-to-charge ratio in a specified two-dimensional area on a sample. However, information of the mass analysis in the depth direction of the sample cannot be obtained. In some studies, an attempt has been made in which a plurality of sample slices are prepared by sequentially slicing one biological sample and the sample slices are sequentially analyzed to obtain three-dimensional mass analysis information.

However, such a method requires an extensive amount of time and labor; therefore, it is impractical. In addition, in attaching each sample slice to a sample plate, it is difficult to attach all the samples to the same position. The difference of their positions makes it difficult to enhance the definition of the mass analysis result image particularly in the depth direction. Additionally, in analyzing a biological sample, a two-dimensional distribution result of mass-to-charge ratios may be first examined and then the position of the following analysis for the depth direction may be determined. In this case, continuous sample slices cannot be prepared in advance, and hence a considerably cumbersome and time-consuming operation will be required.

[Patent Document 1] JP-A 2007-66533
[Patent Document 2] JP-A 2007-157353
[Non-Patent Document 1] Kiyoshi Ogawa and five other authors, "Kenbi Shitsuryo Bunseki Sochi no Kaihatsu," ("Research and Development of Mass Microscope") *Shimadzu Review*, Shimadzu Corporation, Mar. 31, 2006, vol. 62, nos. 3•4, pp. 125-135
[Non-Patent Document 2] Takahiro Harada and eight other authors, "Kenbi Shitsuryo Bunseki Sochi ni yoru Seitai Soshiki Bunseki," ("Biological Tissue Analysis using Mass Microscope") *Shimadzu Review*, Shimadzu Corporation, Apr. 24, 2008, vol. 64, nos. 3•4, pp. 139-146

DISCLOSURE OF THE INVENTION

Problem to be Solved by the Invention

The present invention has been developed in view of the aforementioned problems, and the objective thereof is to provide a mass spectrometer capable of easily and efficiently obtaining, not only two-dimensional mass information mainly on a biological sample or other sample, but three-dimensional mass analysis information in which the mass information is extended also in the depth direction.

Means for Solving the Problem

To solve the aforementioned problem, the present invention provides a mass spectrometer including:

a) a sample holder for holding a sample;

b) an observation unit for observing a surface of the sample held by the sample holder;

c) an ionization unit for ionizing a component at a specified position on the sample held by the sample holder;

d) a mass analyzer for mass analyzing an ion generated by the ionization unit;

e) a sample cutter for cutting a portion of the sample held by the sample holder to expose a sample analysis surface which is a target of an ionization by the ionization unit; and f) a moving unit for moving the sample holder in such a manner that the sample is sequentially carried to an observation position where the sample can be observed by the observation unit, a cutting position where the sample is cut by the sample cutter, and an analysis position where an ionization can be performed by the ionization unit.

In the case where the MALDI method or one of other various kinds of laser desorption ionization (LDI) methods is used as the ionization method, the ionization unit is a unit for delivering a laser light with a micro diameter to a sample. In the case where the secondary ion mass spectrometry method is used, the ionization unit is a unit for delivering a primary ion beam to a sample. In the case where the desorption electrospray ionization method is used, the ionization unit is a nozzle or other device for spraying solvent ions onto a sample. The observation unit may be designed to perform a magnifying observation or a microscopic observation.

In the mass spectrometer according to the present invention, a mass analysis may be performed by the mass analyzer while the specified position where an ionization is performed by the ionization unit is two-dimensionally changed on the sample, whereby a two-dimensional distribution of molecules is obtained.

In a preferable embodiment of the mass spectrometer according to the present invention, the mass spectrometer may further include a controller for controlling the moving unit, the sample cutter, the ionization unit, and the mass analyzer in such a manner as to repeat a plurality of times the process of: cutting a portion of the sample by the sample cutter; ionizing the partially cut sample; and a mass analysis, and the mass analysis information on a plurality of sample analysis surfaces at different positions in a depth direction of the sample may be collected.

In performing an analysis by using the mass spectrometer according to this embodiment, an analysis operator sets a biological sample or other sample in the sample holder such as a sample stage. It is not necessary to slice the sample in advance as in a conventional apparatus; the sample with a certain amount of thickness can be set to the sample holder without being sliced. Then, the sample holder is first moved by the moving unit under the control of the controller, so that the sample is moved to the observation position for the observation unit. In this state, a magnified image of the entirety or a portion of the sample surface can be obtained by the observation unit. Then, while looking at the image, the analysis operator specifies, for example, a two-dimensional measurement area of interest. When the measurement area is determined, the sample holder is moved by the moving unit under the control of the controller, and the sample is moved to the analysis position.

Then, a laser light for example is delivered by the ionization unit to a predetermined measurement point in the measurement area which was specified by the analysis operator based on the image of the sample surface previously obtained by observation. At the point onto which the laser light is delivered, components in the sample are ionized and the generated ions are introduced into the mass analyzer. In the mass analyzer, a variety of methods for separating ions in accordance with their mass-to-charge ratio (m/z) may be used. In order to achieve a high mass-resolving power, a time-of-flight mass analyzer may be preferably used. In the measurement area, the position onto which the laser light is delivered is changed, and a mass analysis is performed every time the position onto which the laser light is irradiated is changed, whereby a two-dimensional mass analysis across the entire measurement area is accomplished.

After the mass analysis is finished, under the control of the controller, the sample holder is moved from the analysis position to the cutting position by the moving unit, where the sample cutter shears off the surface of the sample with a predetermined thickness. This creates a fat surface exposing a portion which has been inside the sample, and this flat surface will be the subsequent sample analysis surface. After the sample holder is moved from the cutting position to the analysis position by the moving unit, a mass analysis is performed for the analysis area in the sample analysis surface which has been previously specified by the analysis operator for example. In the same manner, by repeating the operation of cutting off the sample analysis surface for which an analysis was already performed by the sample cutter and performing a mass analysis for the newly exposed sample analysis surface, the mass analysis information on two-dimensional areas of deep portions in the depth direction can be obtained in a stepwise fashion.

In the manner as just described, without removing the sample from the apparatus in the course of the analysis and without performing a pretreatment such as sequentially slicing the sample and attaching the slices to sample plates, it is possible to collect the mass analysis information on a solid body formed by straightly projecting a predetermined two-dimensional measurement area on the sample onto each in the depth direction, i.e. information on a three-dimensional region of the sample. Particularly, in repeating an ionization of the partially cut sample and a mass analysis a plurality of times, the accuracy of the obtained three-dimensional distribution of molecules can be increased by repeating the mass analysis of two-dimensional areas horizontally at the same position. The positional resolution of the mass analysis information in the depth direction (i.e. spatial resolution) of the sample is determined by the thickness of the sample cut off by a single cutting. Hence, the thickness of the sample cut off at one time may be set to be thin in order to achieve a high positional resolution in the depth direction.

In the case where the ionization unit performs an ionization with the MALDI method, it is necessary to apply a matrix to the measurement point in a measurement area on a sample analysis surface. Given this factor, in the mass spectrometer according to the present invention, it is preferable that the mass spectrometer further includes a matrix supplier for applying a matrix to the sample analysis surface of the sample from which a portion was cut off by the sample cutter.

The matrix supplier drops or sprays a matrix onto the sample so that the matrix is attached to the measurement area previously specified by the analysis operator. When the analysis operator specifies a measurement area on a sample surface image by using a specifier, the measurement area can be obtained, for example, as position (coordinate) information of the sample holder. Hence, the controller uses the position information to control the moving unit in such a manner that the predetermined position in the sample is accurately located at the position where the matrix is supplied by the matrix supplier. Consequently, the matrix supplier can apply a matrix to the specified measurement area with high positional accuracy.

Effects of the Invention

With the mass spectrometer according to the present invention, it is possible to collect not only two-dimensional mass analysis information on a sample but also the mass analysis information for the depth direction thereof, without removing the sample which is set in the sample holder such as a sample stage, and furthermore, without performing a pretreatment outside the apparatus such as slicing the sample or other operations. Consequently, the three-dimensional mass analysis information can be effectively obtained. In addition, the position of the sample on the sample holder does not change before and after a portion of the sample is cut off. This prevents a positional error in the mass analysis information for the depth direction, allowing a creation of a high-resolution three-dimensional mass analysis image.

The thickness of the cutting of a portion of the sample by the sample cutter can be determined by the analysis operator in consideration of the previously obtained mass analysis information or by an automatic determination based on the mass analysis information. Hence, by appropriately changing the thickness of the cutting in accordance with the state of the sample (e.g. in the case where an abnormality such as a lesion is observed), the mass analysis information for the depth direction can be obtained with an accurate positional resolution.

In the case where the matrix supplier is provided, a matrix can be applied to the analysis surface of the sample after a portion is cut off from the sample. This enables a collection of three-dimensional mass analysis information with high analytical sensitivity.

EXPLANATION OF NUMERALS

1 ... Airtight Chamber
2 ... Sample Stage
3 ... Sample Plate
4 ... Sample
5 ... Guide
6 ... Driving Mechanism
7 ... Imaging Unit
8 ... Transmission Light Unit
9 ... Cutter
10 ... Cutter Drive Mechanism
11 ... Laser Light Emitter
12 ... Laser Condensing Optical System
13 ... Matrix Ejector
20 ... Vacuum Chamber
21 ... Vacuum Pump
22 ... Ion Transport Tube
23 and 24 ... Ion Transport Optical System
25 ... Ion Trap
26 ... Time-Of-Flight Mass Analyzer
27 ... Detector
30 ... Data Processor
31 ... Analysis Controller
32 ... Controller
33 ... Stage Driver
34 ... Image Processor
35 ... Cutter Driver
36 ... Laser Driver
37 ... Operation Unit
38 ... Display Unit
39 ... Matrix Application Driver
40 ... Atmospheric Pressure Chamber
41 ... Preparatory Exhaust Chamber
42 and 43 ... Partition Wall
44 ... Partition Wall-Guide Driver
45 ... Vacuum Chamber
A ... Observation Position
B ... Sample Cutting Position
C ... Analysis Position
D ... Matrix Application Position
E ... Waiting Position

BEST MODE FOR CARRYING OUT THE INVENTION

First Embodiment

Figure 1:
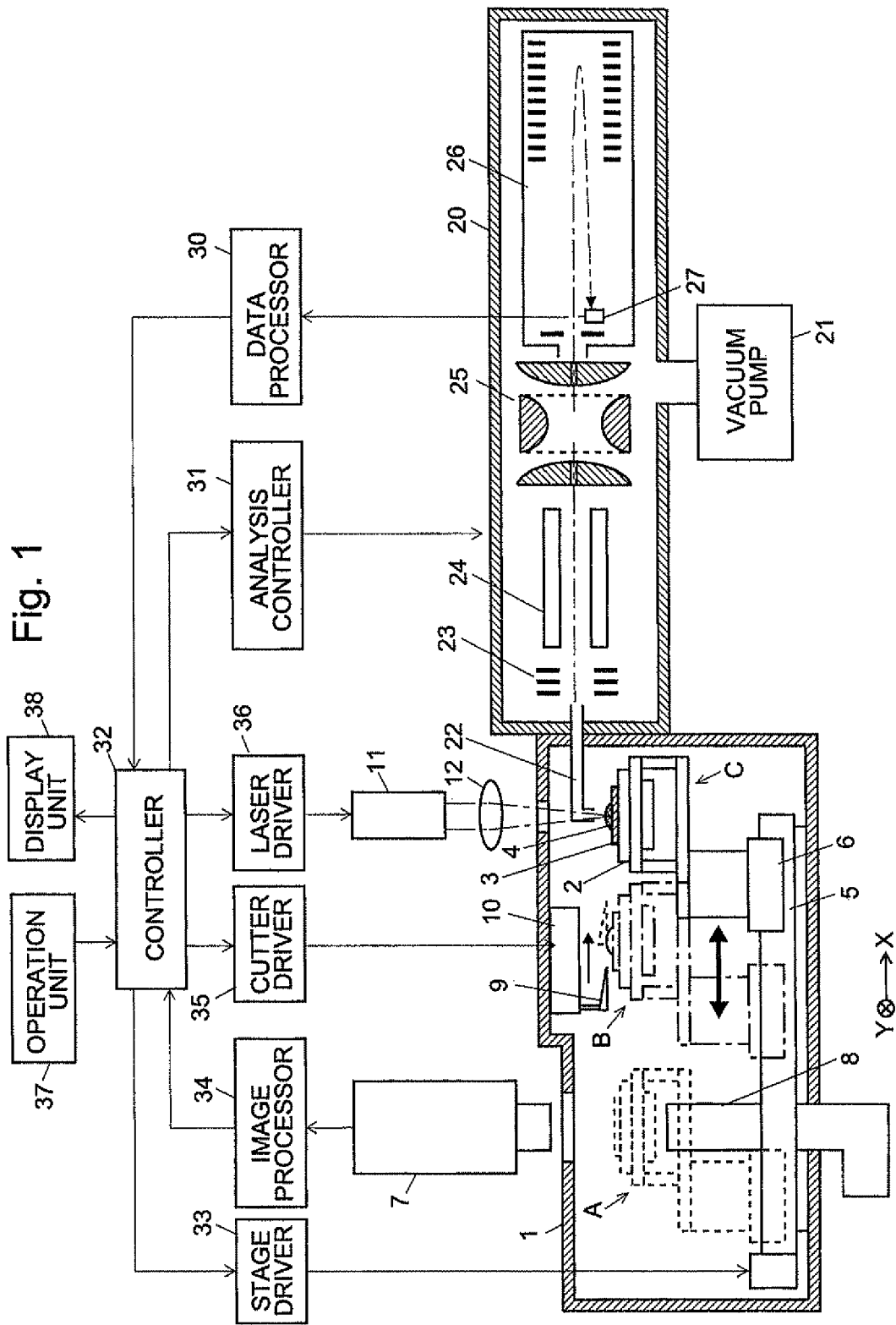
FIG. 1 is an overall configuration diagram of a mass microscope according to the first embodiment of the present invention.

A mass microscope which is an embodiment (a first embodiment) of the mass spectrometer according to the present invention will be described with reference to FIGS. 1 and 2A-2F. FIG. 1 is an overall configuration diagram of the mass microscope according to the first embodiment and FIGS. 2A-2F are schematic diagrams for explaining an example of the operation of the mass microscope according to the first embodiment.

This mass microscope includes an airtight chamber 1 inside of which is maintained in an approximately atmospheric pressure and a vacuum chamber 20 inside of which is maintained at a high-vacuum atmosphere by a vacuum pump 21 such as a turbo molecular pump. In the airtight chamber 1, a sample stage 2 for holding a sample plate 3 on which a sample 4 is placed is provided in such a manner that the sample stage 2 can reciprocally slide in the X-direction along a guide 5. In FIG. 1, the position C where the sample stage 2 is shown with solid lines is the analysis position, the position A with dashed lines is the observation position, and the position B with alternate long and short dash lines is the sample cutting position. By a driving mechanism 6 including a motor and other parts, the sample stage 2 can move within a predetermined range not only in the X-direction along the guide 5, but also in the Y-direction, which is horizontally orthogonal to the X-direction, and in the height direction, i.e. Z-direction.

An imaging unit 7 such as a charge coupled device (CCD) camera is provided outside the airtight chamber 1, over the observation position A. A transmission lighting unit 8 is provided inside the airtight chamber 1 in such a manner as to face the imaging unit 7. When the sample stage 2 is at the observation position A, a light emitted from the transmission light unit 8 illuminates the lower surface of the sample 4 through an opening formed in the sample stage 2, so that the a sample image formed by the transmitted light can be observed by the imaging unit 7. The imaging unit 7, which serves as the observation unit in the present invention, is designed to be capable of performing a magnifying observation or a microscopic observation. The image signals obtained by the imaging unit 7 are sent to an image processor 34, which processes those image signals to form a two-dimensional surface image that can be displayed in a display unit 38 which will be described later. In addition to such a lighting unit for transmission observation, a lighting unit for reflection observation or fluorescence observation may also be provided as a matter of course. In place of the imaging unit 7, an optical microscope which an analysis operator can directly look in may be used for a microscopic observation of the sample 4.

A cutter 9 which moves in the X-Y plane by a cutter drive mechanism 10 including a motor and other parts is provided over the sample cutting position B. When the cutter 9 is driven, with the sample stage 2 on which the sample 4 is placed being at the sample cutting position B and with the height of the sample stage 2 being appropriately adjusted, a piece with a predetermined thickness is cut off from the upper surface of the sample 4 (refer to FIG. 2A). This exposes a sample analysis surface (e.g. 4a in FIG. 2B), which is parallel to the X-Y plane, on the upper surface of the sample 4 remaining on the sample stage 2.

A laser light emitter 11 and a laser condensing optical system 12 are provided over the analysis position C, outside the airtight chamber 1, in order to provide a laser light with a micro diameter onto the surface of the sample 4 so that components contained in the sample 4 are ionized by an atmospheric pressure laser desorption ionization (AP-LDI) method. In the airtight chamber 1, an ion collection opening of an ion transport tube 22 faces the sample 4 to transport ions generated from the sample 4 in response to an irradiation with the laser light.

The airtight chamber 20 contains the following devices: ion transport optical systems 23 and 24 for sending ions into the subsequent stage while converging them; an ion trap 25 for temporarily storing ions; a reflectron time-of-flight mass analyzer 26 for separating ions in accordance with their mass-to-charge ratio (m/z); and a detector 27 for detecting ions separated in the time-of-flight mass analyzer 26. The ion trap 25 is capable of not only holding ions but also selecting ions having a specific mass-to-charge ratio among a variety of introduced ions as precursor ions and dissociating them by a collision induced dissociation to generate product ions. Hence, this mass microscope can perform an MS/MS analysis or an MS$^n$ analysis, in addition to a normal (i.e. without a dissociation operation) mass analysis.

The detection signal produced by the detector 27 is sent to a data processor 30, where the flight time of each ion is converted into a mass-to-charge charge ratio to create a mass spectrum. One mass spectrum is obtained for each of the different measurement points within the measurement area. Then, a mass analysis result image or other information for a specific mass-to-charge ratio is created based on the obtained mass spectra.

The controller 32 for managing the overall control of the mass microscope controls the operation of a mass analyzer such as the ion trap 25 through an analysis controller 31, the movement of the sample stage 2 with the drive unit 6 through a stage driver 33, the emission of a laser light from the laser light emitter 11 through a laser driver 36, and the operation of the cutter 9 through a cutter driver 35 and the cutter drive mechanism 10. An operation unit 37 for allowing an analysis operator to operate and enter directions and a display unit 38 for displaying a two-dimensional observation image of the sample 4, a mass analysis result image as a mass analysis result, or other data are connected to the controller 32.

At least a portion of the functions of the controller 32, the analysis controller 31, and the data processor 30 can be realized by executing dedicated software installed in a personal computer.

A typical example of the procedure of a measurement using the mass microscope according to the first embodiment will be described.

The analysis operator first places the sample 4 to be measured on the sample plate 3 outside the airtight chamber 1, and sets the sample plate 3 on the sample stage 2. The sample 4 may be a biological sample such as the brain of a mouse, but there is no need to slice it in advance: it is only necessary to place the thick sample 4, without slicing it, on the sample plate 3 and set them on the sample stage 2.

When the analysis operator enters an instruction for performing a microscopic observation through the operation unit 37, the controller 32 receives the instruction and moves the sample stage 2 to the observation position A through the stage driver 33 and the driving mechanism 6. When the sample stage 2 reaches the observation position A, the imaging unit 7 focuses on the sample 4 at an indicated magnification and takes a surface observation image of the sample 4 on the sample stage 2. The controller 32 displays the magnified image of the surface of the sample 4 created by the image processor 34 on a window of the display unit 38.

At this point in time, the observation image is displayed on the display unit 38 as a real-time image. Looking at the observation image, the analysis operator performs an operation through the operation unit 37 to change the observation magnification and/or move the sample stage 2 so that an observation image of an appropriate two-dimensional area on the sample 4 is displayed. In this manner, the analysis operator determines a measurement area (or measurement point) to be analyzed on the sample 4, and specifies it through the operation unit 37. For example, the measurement area can be specified by moving a cursor to a desired position and performing a click operation or by encompassing a desired area on the magnified image of the sample 4 displayed on the display unit 38. The specified measurement area is memorized in the controller 32 as a coordinate position on the sample stage 2.

When the measurement area is determined, the controller 32 moves the sample stage 2 from the observation position A to the analysis position C through the stage driver 33 and the driving mechanism 6. After the sample stage 2 is moved to the analysis position C, the controller 32 finely adjusts the position of the sample stage 2 in the X-direction and Y-direction, and also in the Z-direction to the optimum height so that a laser light will be delivered to the first measurement point in the measurement area which was previously memorized as the coordinate position. Then, the controller 32 controls the laser light emitter 11 through the laser driver 36 so as to emit a laser light for a short period of time, so that the laser light is delivered onto the intended measurement point on the sample 4.

The delivered laser light ionizes the components in the sample 4. The generated ions are drawn into the ion collection opening of the ion transport tube 22, through which they are introduced into the vacuum chamber 20. The ions are introduced into the ion trap 25 through the ion transport optical systems 23 and 24. After a cooling or other type of operation is performed in the ion trap 25, a kinetic energy is given to the ions almost collectively and the ions are sent into the time-of-flight mass analyzer 26. Generally, in the LDI, the number of ions generated by one irradiation with laser light is not that large, and the amount of the generated ions varies significantly. Given these factors, a pulsed laser light is delivered a plurality of times onto the same measurement point, and the ions generated by each irradiation are temporarily stored in the ion trap 25. Then, the ions are collectively mass analyzed in the time-of-flight mass analyzer 26.

The ions collectively ejected from the ion trap 25 are separated in accordance with their mass-to-charge ratio during their flight in the time-of-flight mass analyzer 26, and reach the detector 27 at different points in time. The detector 27 provides a detection signal corresponding to the amount of incident ions and the detection signal is sent to the data processor 30. Since the flight time of each ion corresponds to its mass-to-charge ratio, the data processor 30 converts the flight time into the mass-to-charge ratio to create a mass spectrum.

The controller 32 controls the driving mechanism 6 through the stage driver 33 in such a manner that the irradiation position of the laser light is sequentially moved in the X-direction and Y-direction by a predetermined step width in the measurement area. By performing the mass analysis as previously described while changing the scanning position of the delivered laser light, the data processor 30 creates a mass spectrum for each measurement point. In addition, the data processor 30 performs a qualitative or quantitative analysis based on these mass spectra to identify the substance or deduce the content thereof.

In mass analyzing a predetermined measurement area on the sample 4, the signal intensity of a specific mass-to-charge ratio is obtained every time the laser irradiation position is changed as previously described. By producing a two-dimensional image from the signal intensities, a mass analysis result image for a specific mass-to-charge ratio can be created. The controller 32 displays the mass analysis result obtained in the manner as just described on a window of the display unit 38.

After the mass analysis for the specified measurement area is finished, the controller 32 moves the sample stage 2 to the sample cutting position B through the stage driver 33 and the driving mechanism 6.

Figure 2A:
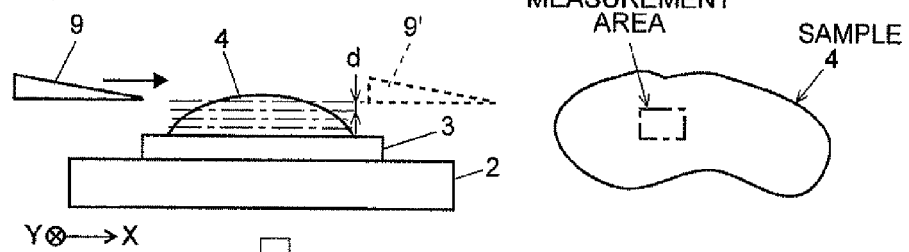
FIGS. 2A-2F are schematic diagrams for explaining an example of the operation of the mass microscope according to the first embodiment.
Figure 2B:
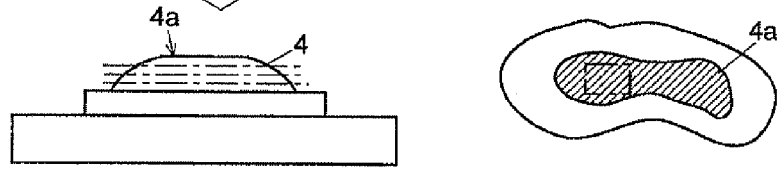
Figure 2C:
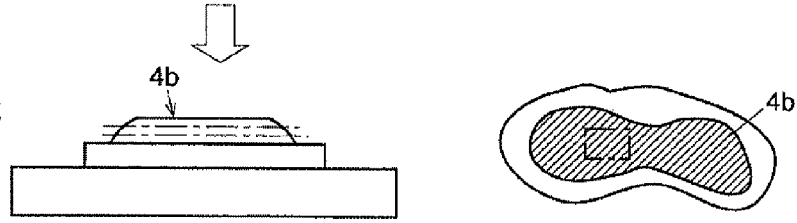
Figure 2D:
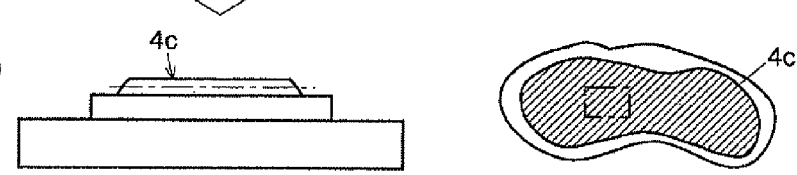
Figure 2E:

After the sample stage 2 is moved to the sample cutting position B, the controller 32 controls the cutter drive mechanism 10 through the cutter driver 35 so as to horizontally move the cutter 9. Consequently, as shown in FIG. 2B, a portion of the sample 4 is cut by a thickness of d from the upper surface, exposing a portion which was hidden inside the sample 4. This portion is set as a subsequent sample analysis surface 4a. The cutting thickness d can be specified beforehand by the analysis operator through the operation unit 37, and in accordance with the specified value, the movement of the sample stage 2 in the Z-direction or the movement of the cutter 9 in the Z-direction is adjusted to change the actual cutting thickness d. When the same sample is cut a plurality of times as in this example, the same thickness d may be set for every cutting, or the cutting thickness may be changed for each two-dimensional mass analysis.

After the cutting of the sample as previously described is finished, the controller 32 moves the sample stage 2, through the stage driver 33 and the driving mechanism 6, form the sample cutting position B to the analysis position C. The controller 32 performs a mass analysis for the measurement area which was memorized beforehand as a coordinate position and for which the first measurement was already performed before the sample 4 was cut. After a two-dimensional mass analysis for the measurement area on the sample analysis surface 4a is terminated, the sample stage 2 is sent again to the sample cutting position B and a portion with a predetermined thickness of d is cut off below the sample analysis surface 4 by the cutter 9. Consequently, a new sample analysis surface 4b is exposed, and a two-dimensional mass analysis is performed for the measurement area on the sample analysis surface 4b. In this manner, for the measurement area that was initially specified by the analysis operator, a two-dimensional mass analysis result image of the sample 4 can be created for each slicing position in the depth direction, i.e. in the height direction or Z-direction (refer to FIGS. 2C through 2E).

Figure 2F:
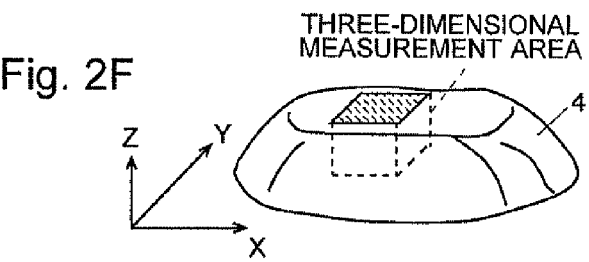

The sample 4 remains on the sample stage 2; it does not move on the sample stage 2 even after it is partially cut off by the cutter 9. In addition, the measurement area or the measurement position specified by the analysis operator is handled as the coordinate information on the sample stage 2. Therefore, even though a two-dimensional mass analysis and the cutting of a portion of the sample 4 are repeated a plurality of times, it is always possible to obtain a mass analysis result image for the same measurement area. That is, the aforementioned measurement corresponds to collecting the mass distribution information of an approximately rectangular parallelepiped portion (which becomes an exact rectangular parallelepiped if the top surface is flat) in the sample 4 as shown in FIG. 2F. By combining a plurality of mass analysis result images, a three-dimensional mass analysis imaging data can be obtained.

As just described, in the mass microscope of the present embodiment, the analysis operator has only to set the sample 4 on the sample stage 2 and determine a measurement point or measurement area based on a clear observation image. Then, without the need to remove the sample 4 from the sample stage 2, a three-dimensional mass analysis imaging data for a predetermined portion in the sample 4 can be obtained. This improves the measurement efficiency by freeing the analysis operator from the cumbersome task of slicing the sample 4 and attaching them onto the sample plate. Further, since the sample 4 is progressively cut without being removed from the sample stage 2, no change in the position of the sample 4 occurs during the analysis and an accurate alignment in the horizontal direction between layers (i.e. between the mass analysis result images for two sample surfaces separated by a cut slice), which has been conventionally difficult, can be performed. Thus, a detailed mass analysis imaging data can be obtained.

In the aforementioned embodiment, after a microscopic measurement is performed and a measurement point or a measurement area is determined at the observation position A, a mass analysis at the analysis position C and a cutting of a portion of the sample 4 at the sample cutting position B are repeated. However, the sample stage 2 may be moved to the observation position A every time a portion of the sample 4 is cut off, and the microscopic image of the newly exposed sample analysis surface may be taken. The microscopic image of the sample 4 taken after every cutting can be stored in an image memory of the controller 32 so that the microscopic images can later be compared with each other or with a two-dimensional mass analysis result image.

In the aforementioned embodiment, the atmospheric pressure laser desorption ionization (AP-LDI) method is used as an ionization method. However, other atmospheric pressure ionization methods can also be used, such as a desorption electrospray ionization (DESI) method or an electrospray-assisted laser desorption ionization (ELDI) method.

Second Embodiment

Figure 3:
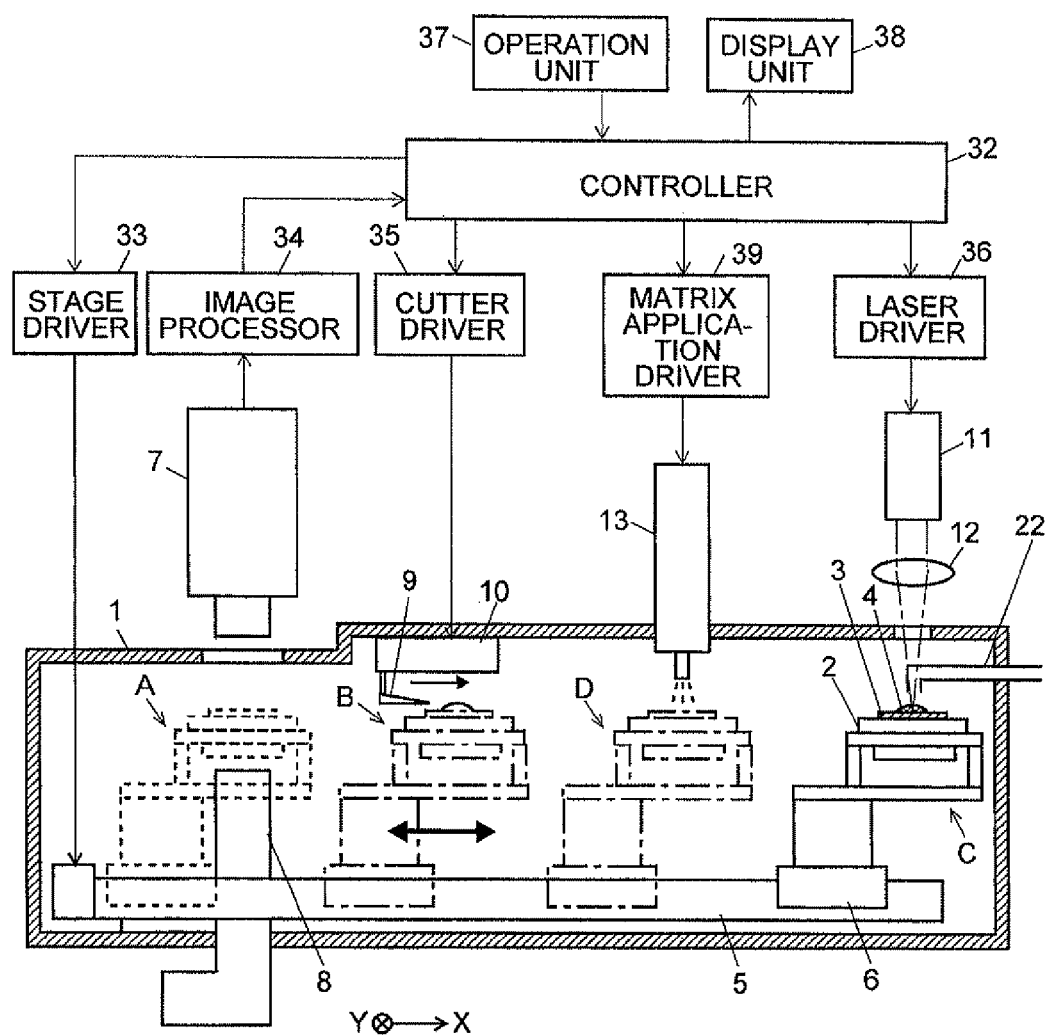
FIG. 3 is an overall configuration diagram of a mass microscope according to the second embodiment of the present invention.

Next, a mass microscope according to another embodiment (a second embodiment) of the present invention will be described with reference to FIG. 3. FIG. 3 is an overall configuration diagram of the mass microscope according to the second embodiment, and the illustration of the vacuum chamber 20 which is shown in FIG. 1 is omitted. For the components shown in FIG. 3, the same or corresponding components as in FIG. 1 are indicated with the same numerals and the explanations are omitted.

In the mass microscope of the second embodiment, an ionization is performed by an atmospheric pressure MALDI method. In the MALDI method, it is necessary to apply a matrix on a sample surface for which an ionization is performed. Hence, a matrix application position D is provided between the sample cutting position B and the analysis position C. A matrix ejector 13 having a microscopic nozzle for ejecting a matrix is provided over the matrix application position D. The matrix ejector 13 is driven by a matrix application driver 39 and capable of applying a matrix to any position on the sample 4.

In this mass microscope, after a microscopic measurement of the sample 4 is performed and a measurement area is determined at the measurement point A, as well as after a portion of the sample 4 is cut off at the sample cutting position B and before a mass analysis is performed at the analysis position C, the controller 32 moves the sample stage 2 to the matrix application position D through the stage driver 33 and the driving mechanism 6. Further, the controller 32 adjusts the position of the sample stage 2 in the X-direction and Y-direction and also adjusts its position in the Z-direction to optimize the height in order that a matrix is applied to the measurement area (or measurement point) which is memorized as a coordinate position. Then, an appropriate amount of matrix is ejected from the matrix ejector 13 to the sample 4 through the matrix application driver 39, so that the matrix is applied to the predetermined position on the surface of the sample 4. When the matrix is to be applied to a certain amount of measurement area, the sample stage 2 may be minutely moved in the X-direction and Y-direction while the matrix is continuously or intermittently ejected from the matrix ejector 13.

After the matrix is applied to the measurement area on the sample 4 or to the measurement area on the sample analysis surface which was exposed by a cutting process, the sample stage 2 is moved from the matrix application position D to the analysis position C and a mass analysis is performed as in the first embodiment. Since higher analysis sensitivity is achieved by the MALDI method compared to the LDI method which uses no matrix, a more accurate mass analysis result image can be obtained.

Third Embodiment

Figure 4:
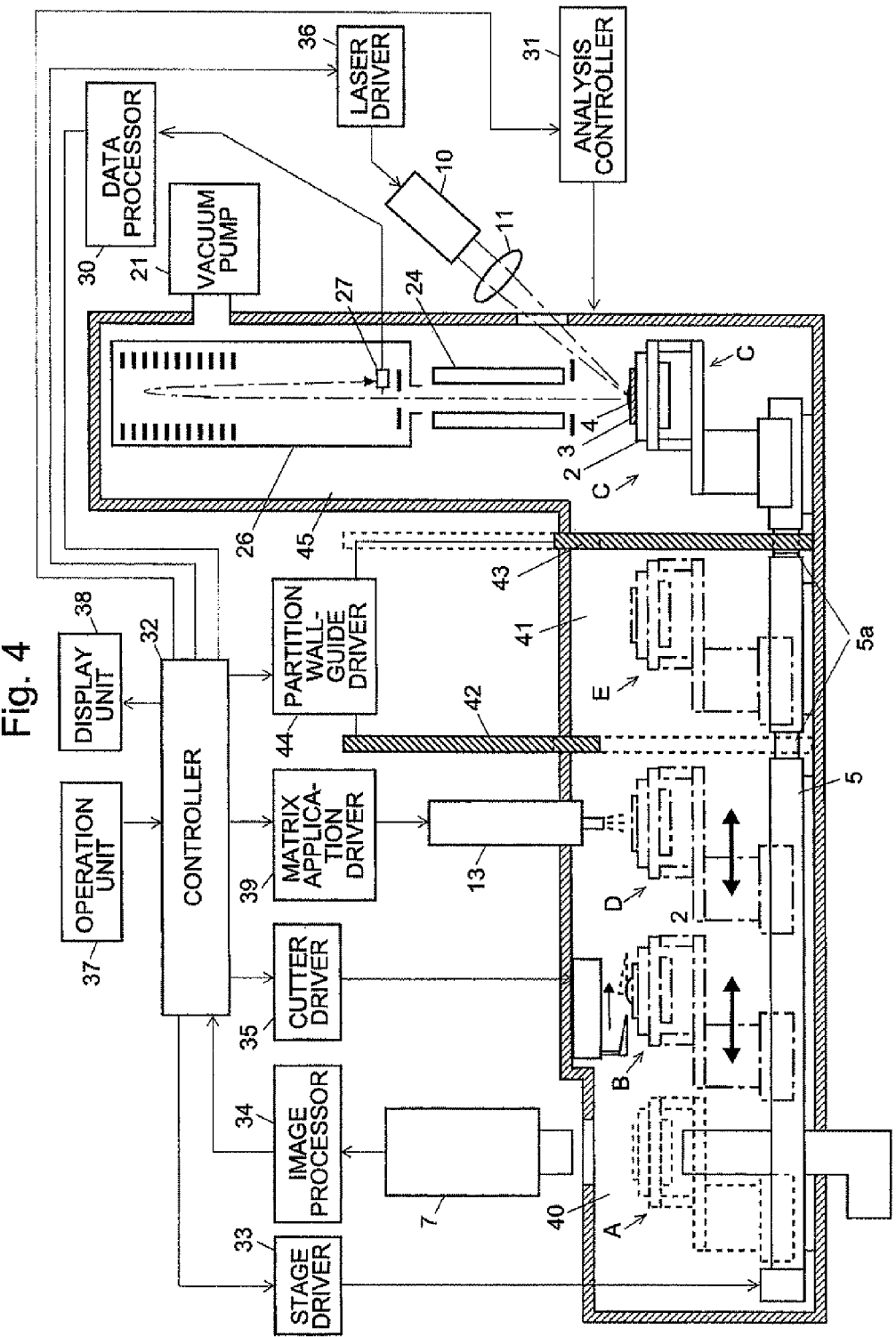
FIG. 4 is an overall configuration diagram of a mass microscope according to the third embodiment of the present invention.

Next, a mass microscope according to another embodiment (a third embodiment) of the present invention will be described with reference to FIG. 4. FIG. 4 is an overall configuration diagram of the mass microscope of the third embodiment. The same components as in the first embodiment shown in FIG. 1 are indicated with the same numerals and the explanations are omitted.

In the mass microscopes of the first and second embodiments, an ionization is performed in the airtight chamber 1, i.e. under atmospheric pressure, whereas in the mass microscope of the third embodiment, an ionization by the MALDI method is performed in a vacuum atmosphere. That is, as opposed to the second embodiment in which the AP-MALDI is used, the mass microscope of the third embodiment uses the vacuum MALDI.

Even when the MALDI method is performed in a vacuum atmosphere, the operation of applying a matrix to the sample 4 must be performed under atmospheric pressure. In the case where a biological sample is used, it is preferable that a microscopic observation and cutting of the sample are performed under atmospheric pressure in order to prevent the sample from drying or other problems. Given this factor, in the mass microscope of the third embodiment, a preparatory exhaust chamber 41 is provided between the atmospheric pressure chamber 40 in which the observation position A, the sample cutting position B, and the matrix application position D are provided and a vacuum chamber 45 in which the analysis position C and the mass analyzer such as a time-of-flight mass analyzer 26 and other units are provided. The preparatory exhaust chamber 41 has a first partition wall 42 and a second partition wall 43 on both sides. Each of the two walls can be opened and closed.

When the second partition wall 43 is closed and the first partition wall 42 is opened by the controller 32 through a partition wall-guide driver 44, the preparatory exhaust chamber 41 communicates with the atmospheric pressure chamber 40. On the other hand, when the first partition wall 42 is closed and the second partition wall 43 is opened, the preparatory exhaust chamber 41 communicates with the vacuum chamber 45. Portions of the guide 5 are designed to be a retractable guide 5a which is driven while interlocking with the partition wall 42 or 43. That is, when the partition wall 42 or 43 is opened, the corresponding guide 5a is pulled out to connect the guides of the two chambers across the partition wall, and when the partition wall 42 or 43 is closed, both guides 5a are withdrawn so as not to impede the closing operation. Of course, the guide 5 may have another structure such as a bending mechanism other than the withdrawable mechanism.

In the mass microscope of the third embodiment, after a matrix is applied to the sample 4 at the matrix application position D, the sample stage 2 is moved to a waiting position E. In this state, both of the partition walls 42 and 43 are closed and the preparatory exhaust chamber 41 is sealed. Then, the inside of the preparatory exhaust chamber 41 is evacuated by a vacuum pump (not shown). When the degree of vacuum is increased to some extent, the second partition wall 43 is opened and the sample stage 2 is moved to the analysis position C. Since the internal space of the preparatory exhaust chamber 41 is sufficiently small compared to the vacuum chamber 45, the process of evacuating the preparatory exhaust chamber 41 from the atmospheric pressure state to the vacuum state requires only a short period of time. Therefore, the time required for a measurement can be reduced compared to the case where the vacuum state of the vacuum chamber 45 needs to be broken to move the sample stage 2 to the analysis position C.

Fourth Embodiment

Figure 5:
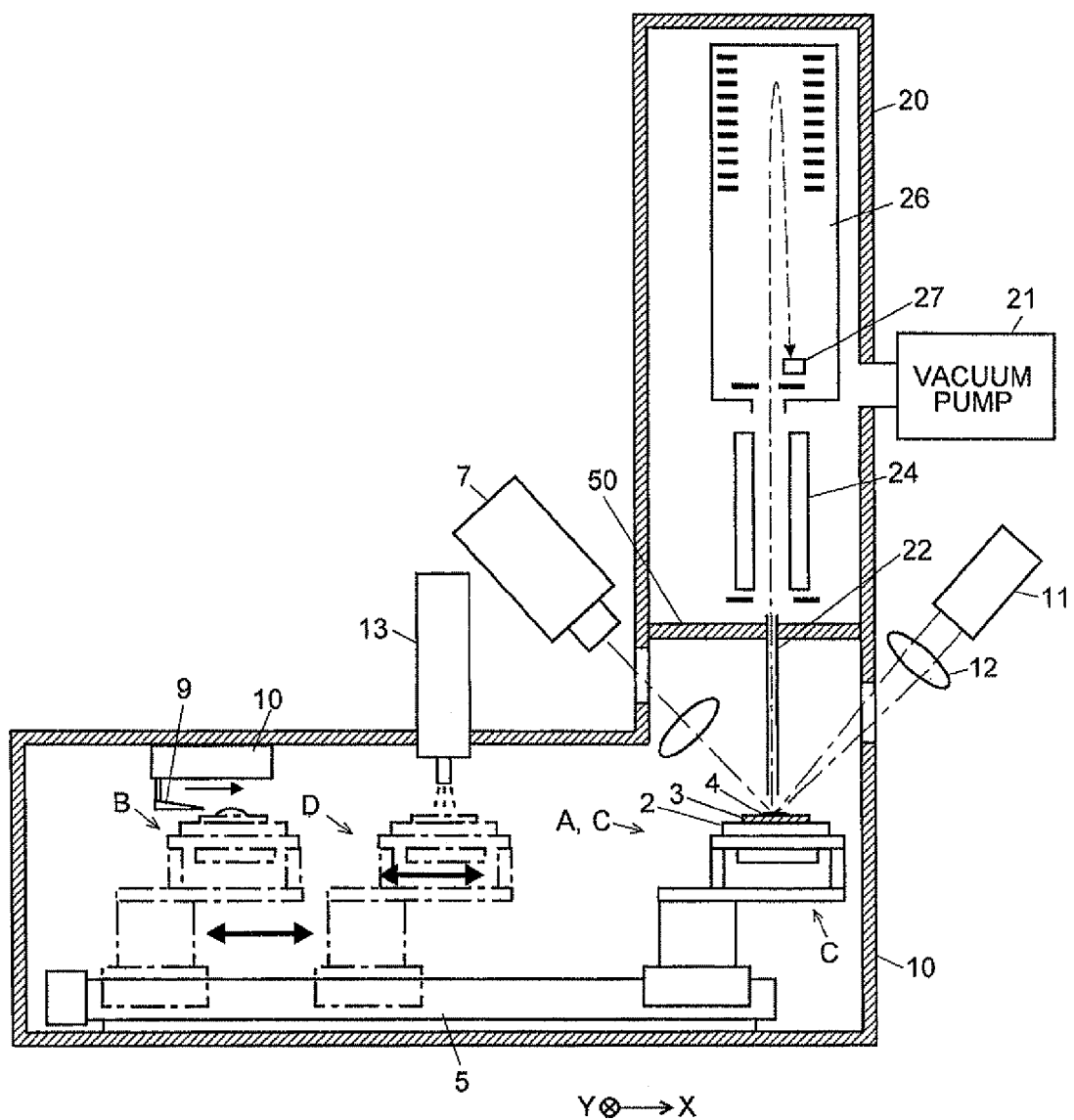
FIG. 5 is an overall configuration diagram of a mass microscope according to the fourth embodiment of the present invention.

A mass microscope according to another embodiment (a fourth embodiment) of the present invention will be described with reference to FIG. 5. FIG. 5 is an overall configuration diagram of the mass microscope of the fourth embodiment. The explanations for the control system and signal processing system are omitted.

In the first through third embodiments, the analysis position C where a laser light is delivered to the sample 4 and the observation position A where the sampler 4 is observed are located at different positions. In the mass microscope of the fourth embodiment, the analysis position C and the observation position A are the same. That is, while the laser light emitted from the laser emitter 11 is being delivered to the sample 4, the surface observation image of the sample 4 can be taken by the imaging unit 7. The operation of analyzing a target sample is basically the same as in the second embodiment.

If the laser light is obliquely delivered to the sample 4 as shown in FIG. 5, the height of the sample analysis surface must be stabilized to perform a mass analysis for the same measurement area or measurement point. Therefore, it is preferable that, at the analysis position C, the sample stage 2 is elevated in the Z-direction by the cutting thickness d as the sample 4 is sequentially cut off from its upper surface and becomes thinner as shown in FIGS. 2A-2F.

It should be noted that the embodiment described thus far is merely an example of the present invention, and it is evident that any modification, adjustment, or addition appropriately made within the spirit of the present invention is also included in the scope of the claims of the present application.

The invention claimed is:

1. A mass spectrometer comprising:
a sample holder for holding a sample;
an observation unit for observing a surface of the sample held by the sample holder;
an ionization unit for ionizing a component at a specified position on the sample held by the sample holder;
a mass analyzer for mass analyzing an ion generated by the ionization unit;
a sample cutter for cutting a portion of the sample held by the sample holder to expose a sample analysis surface which is a target of an ionization by the ionization unit;
a moving unit for moving the sample holder in such a manner that the sample is sequentially carried to an observation position where the sample can be observed by the observation unit, a cutting position where the sample is cut by the sample cutter, and an analysis position where an ionization can be performed by the ionization unit; and a controller for controlling the moving unit, the sample cutter, the ionization unit, and the mass analyzer in such a manner as to repeat a plurality of times a process of cutting a portion of the sample by the sample cutter, ionizing the partially cut sample, and a mass analysis, wherein:

mass analysis information on a plurality of sample analysis surfaces at different positions in a depth direction of the sample is collected.

2. The mass spectrometer according to claim 1, wherein:
a mass analysis is performed by the mass analyzer while the specified position where an ionization is performed by the ionization unit is two-dimensionally changed on the sample to obtain a two-dimensional distribution of molecules.

3. The mass spectrometer according to claim 2, wherein:
the ionization unit performs a matrix-assisted laser desorption ionization; and
the mass spectrometer further comprises a matrix supplier for applying a matrix to the sample analysis surface of the sample from which a portion was cut off by the sample cutter.

4. The mass spectrometer according to claim 1, wherein:
in repeating the process of cutting a portion of the sample by the sample cutter, ionizing the partially cut sample, and a mass analysis a plurality of times, the mass analysis is performed by the mass analyzer while the specified position for which an ionization is performed by the ionization unit is two-dimensionally changed on the sample in a same cut state to obtain a three-dimensional distribution of molecules.

5. The mass spectrometer according to claim 4, wherein:
in repeating the process of ionizing the partially cut sample and a mass analysis a plurality of times, a mass analysis for a two-dimensional area horizontally at a same position is repeated to increase an accuracy of the obtained three-dimensional distribution of molecules.

6. The mass spectrometer according to claim 5, wherein:
the ionization unit performs a matrix-assisted laser desorption ionization; and
the mass spectrometer further comprises a matrix supplier for applying a matrix to the sample analysis surface of the sample from which a portion was cut off by the sample cutter.

7. The mass spectrometer according to claim 4, wherein:
the ionization unit performs a matrix-assisted laser desorption ionization; and
the mass spectrometer further comprises a matrix supplier for applying a matrix to the sample analysis surface of the sample from which a portion was cut off by the sample cutter.

8. The mass spectrometer according to claim 1, wherein:
the ionization unit performs a matrix-assisted laser desorption ionization; and
the mass spectrometer further comprises a matrix supplier for applying a matrix to the sample analysis surface of the sample from which a portion was cut off by the sample cutter.

9. A mass spectrometer comprising:
a sample holder configured to hold a sample;
an observation unit configured to observe a surface of the sample held by the sample holder;
an ionization unit configured to ionize a component at a specified position on the sample held by the sample holder;
a mass analyzer configured to mass analyze an ion generated by the ionization unit;
a sample cutter configured to cut a portion of the sample held by the sample holder to expose a sample analysis surface which is a target of an ionization by the ionization unit;
a moving unit configured to move the sample holder in such a manner that the sample is sequentially carried to an observation position where the sample can be observed by the observation unit, a cutting position where the sample is cut by the sample cutter, and an analysis position where an ionization can be performed by the ionization unit; and
a controller configured to control the moving unit, the sample cutter, the ionization unit, and the mass analyzer in such a manner as to repeat a plurality of times a process of cutting a portion of the sample by the sample cutter, ionizing the partially cut sample, and a mass analysis, wherein:

mass analysis information on a plurality of sample analysis surfaces at different positions in a depth direction of the sample is collected.

10. The mass spectrometer according to claim 9, wherein:
a mass analysis is performed by the mass analyzer while the specified position where an ionization is performed by the ionization unit is two-dimensionally changed on the sample to obtain a two-dimensional distribution of molecules.

11. The mass spectrometer according to claim 10, wherein:
the ionization unit performs a matrix-assisted laser desorption ionization; and
the mass spectrometer further comprises a matrix supplier configured to apply a matrix to the sample analysis surface of the sample from which a portion was cut off by the sample cutter.

12. The mass spectrometer according to claim 9, wherein:
in repeating the process of cutting a portion of the sample by the sample cutter, ionizing the partially cut sample, and a mass analysis a plurality of times, the mass analysis is performed by the mass analyzer while the specified position for which an ionization is performed by the ionization unit is two-dimensionally changed on the sample in a same cut state to obtain a three-dimensional distribution of molecules.

13. The mass spectrometer according to claim 12, wherein:
in repeating the process of ionizing the partially cut sample and a mass analysis a plurality of times, a mass analysis for a two-dimensional area horizontally at a same position is repeated to increase an accuracy of the obtained three-dimensional distribution of molecules.

14. The mass spectrometer according to claim 13, wherein:
the ionization unit performs a matrix-assisted laser desorption ionization; and
the mass spectrometer further comprises a matrix supplier configured to apply a matrix to the sample analysis surface of the sample from which a portion was cut off by the sample cutter.

15. The mass spectrometer according to claim 12, wherein:
the ionization unit performs a matrix-assisted laser desorption ionization; and
the mass spectrometer further comprises a matrix supplier configured to apply a matrix to the sample analysis surface of the sample from which a portion was cut off by the sample cutter.

16. The mass spectrometer according to claim 9, wherein:
the ionization unit performs a matrix-assisted laser desorption ionization; and the mass spectrometer further comprises a matrix supplier configured to apply a matrix to the sample analysis surface of the sample from which a portion was cut off by the sample cutter.

* * * * *